(12) United States Patent
Schaubhut et al.

(10) Patent No.: US 12,035,917 B2
(45) Date of Patent: Jul. 16, 2024

(54) DEVICES AND METHODS FOR LIGATOR ACTUATION

(71) Applicant: Boston Scientific Scimed, Inc., Maple Grove, MN (US)

(72) Inventors: Andrew J. Schaubhut, Bolton, MA (US); Jeff Gray, Sudbury, MA (US); Nelly Nganga, Lowell, MA (US); Austin K. Schlensker, Marlborough, MA (US); Jenny Dandin, Worcester, MA (US); Ryan Gleason, Clinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 584 days.

(21) Appl. No.: 16/875,092

(22) Filed: May 15, 2020

(65) Prior Publication Data
US 2020/0360022 A1 Nov. 19, 2020

Related U.S. Application Data

(60) Provisional application No. 62/848,742, filed on May 16, 2019.

(51) Int. Cl.
*A61B 17/12* (2006.01)
*A61B 17/00* (2006.01)

(52) U.S. Cl.
CPC ........... *A61B 17/12013* (2013.01); *A61B 2017/00818* (2013.01); *A61B 2017/12018* (2013.01)

(58) Field of Classification Search
CPC .... A61B 17/12013; A61B 2017/00818; A61B 2017/12018; A61B 1/00133;
(Continued)

(56) References Cited

U.S. PATENT DOCUMENTS

2002/0072757 A1* 6/2002 Ahmed ............ A61B 17/12013
606/139
2004/0006256 A1 1/2004 Suzuki et al.
(Continued)

FOREIGN PATENT DOCUMENTS

CN 208404709 U 1/2019
CN 109674512 A 4/2019
(Continued)

OTHER PUBLICATIONS

International Search Report and Written Opinion for Application No. PCT/US2020/033074, mailed Jul. 22, 2020, 30 pages.

*Primary Examiner* — Kelly J Bekker
*Assistant Examiner* — Andrew P. Restaino
(74) *Attorney, Agent, or Firm* — Seager, Tufte & Wickhem, LLP

(57) ABSTRACT

The present disclosure relates generally to ligators, actuation devices, and methods for deploying ligation bands around a portion of tissue, utilizing an endoscope for suction, visualization, and support. In some embodiments, a ligator may include an elongate member having a lumen, and a ligating band dispenser extending from a distal end of the elongate member. The ligating band dispenser may include a cap and at least one ligating band on the cap. The ligator may further include an actuation device extending around the elongate member, wherein the actuation device includes a body, and a bobbin coupled to the body by support arms. A suture may be coupled between the bobbin and the at least one ligating band, wherein rotation of the bobbin draws the suture towards a proximal end of the elongate member to deploy the at least one ligating band from the cap.

14 Claims, 8 Drawing Sheets

(58) Field of Classification Search
CPC ........... A61B 2017/00296; A61B 2017/00407; A61B 2017/00438
See application file for complete search history.

(56) References Cited

U.S. PATENT DOCUMENTS

| | | | |
|---|---|---|---|
| 2006/0252993 A1* | 11/2006 | Freed | A61B 1/0052 604/95.04 |
| 2008/0091218 A1 | 4/2008 | Richardson | |
| 2011/0099773 A1* | 5/2011 | Golden | F16B 2/185 24/457 |
| 2012/0059225 A1* | 3/2012 | Gostout | A61B 17/0218 600/204 |
| 2014/0081294 A1 | 3/2014 | Kamler | |
| 2016/0361066 A1* | 12/2016 | Wolfe | A61B 1/00133 |

FOREIGN PATENT DOCUMENTS

| | | |
|---|---|---|
| EP | 2055247 A1 | 5/2009 |
| WO | 2009086396 A1 | 7/2009 |

\* cited by examiner

DEVICES AND METHODS FOR LIGATOR ACTUATION

CROSS-REFERENCE TO RELATED APPLICATIONS

This application claims the benefit of priority under 35 U.S.C. § 119 to U.S. Provisional Application Ser. No. 62/848,742, filed May 16, 2019, the disclosure of which is incorporated herein by reference in its entirety for all purposes.

FIELD

The present disclosure relates to medical ligating instruments and, more particularly, to actuation devices for endoscopic ligators.

BACKGROUND

For ligating tissue inside a body cavity, orifice, or lumen, physicians may use an endoscope to access and ligate the target tissue. In one such form of endoscopic ligation, physicians may use the endoscope to position a stretched elastic band over the target tissue, and then release the band onto the tissue so the band contracts and engage the tissue. The inward pressure of the band constricts the target tissue, thereby causing the tissue to die and slough off.

It can be difficult for a medical professional, such as a surgeon, to both position the endoscope at the ligation site and deploy elastic bands onto the target tissue. It is therefore common practice for the physician to remove his or her guiding hand from the endoscope patient end shaft in order to deploy a band, potentially losing position. It would therefore be desirable to have an apparatus which enables the surgeon to maintain a hand on the endoscope shaft while simultaneously activating the release of the elastic bands with greater ease.

SUMMARY

The present disclosure in its various embodiments relates generally to ligators, actuation devices, and methods for deploying ligation bands around a portion of tissue, such as a hemorrhoid. In one or more embodiments, a ligator may include an elongate member having a lumen, and a ligating band dispenser extending from a distal end of the elongate member. The ligating band dispenser may include a cap, and at least one ligating band positioned on the cap. The ligator may further include an actuation device extending around the elongate member, the actuation device including a body defining a central cavity for receiving the elongate member, and a bobbin coupled to the body by a set of support arms. The ligator may further include a suture coupled between the bobbin and the at least one ligating band, wherein rotation of the bobbin draws the suture towards a proximal end of the elongate member to deploy the at least one ligating band from the cap. In one or more embodiments, the ligator may further include a second elongate member having a second lumen, wherein the suture extends through the second lumen. In one or more embodiments, the second elongate member is positioned external to the elongate member. In one or more embodiments, the actuation device is coupled to the proximal end of the elongate member. In one or more embodiments, the actuation device may further include at least one support extending into the central cavity, wherein the at least one support may include a contoured surface engaged with an outer surface of the elongate member. In one or more embodiments, the actuation device may further include a gripping ring extending from an exterior surface of the body. In one or more embodiments, the bobbin may include a spooling section including a recess, wherein the suture is received within the recess, and a plurality of angled teeth along a bobbin exterior surface. The bobbin may further include a pin extending from a bobbin sidewall, wherein the pin extends along an axis of rotation of the bobbin, and wherein the pin is rotatably coupled with the set of support arms. In one or more embodiments, the actuation device may include a first free end secured to a second free end by a plurality of locking features extending from a surface of the second free end. In some embodiments, the first free end may include a locking protrusion operable to extend between two adjacent locking features of the plurality of locking features.

In one or more embodiments, an actuation device for an endoscopic ligator may include a body defining a central cavity for receiving an elongate member, at least one support extending into the central cavity from the body, the at least one support engageable with an outer surface of the elongate member. The actuation device may further include a bobbin coupled to the body by a set of support arms, wherein a suture is coupled between the bobbin and a ligating band of a ligating band dispenser, and wherein rotation of the bobbin spools the suture about the bobbin. In one or more embodiments, the body is coupleable to a proximal end of the elongate member. In one or more embodiments, the bobbin may include a spooling section including a recess, wherein the suture is received within the recess, and a plurality of angled teeth along a bobbin exterior surface. The bobbin may further include a pin extending from a bobbin sidewall, wherein the pin extends along an axis of rotation of the bobbin, and wherein the pin is rotatably coupled with the set of support arms. In one or more embodiments, the actuation device may further include a first free end secured to a second free end by a plurality of locking features extending from a surface of the second free end. In one or more embodiments, the first free end may include a locking protrusion operable to extend into a cavity defined by two adjacent locking features of the plurality of locking features. In one or more embodiments, the actuation device may further include a gripping ring extending from an exterior surface of the body.

In one or more embodiments, a method may include providing an elongate member having a lumen, and coupling a ligating band dispenser to a distal end of the elongate member. The ligating band dispenser may include a cap, and at least one ligating band positioned on the cap. The method may further include coupling an actuation device to the elongate member. The actuation device may include a body defining a central cavity for receiving the elongate member and a bobbin coupled to the body by a set of support arms. The method may further include coupling a suture between the bobbin and the at least one ligating band, wherein rotation of the bobbin draws the suture towards a proximal end of the elongate member to deploy the at least one ligating band from the cap. In one or more embodiments, the method may further include providing a second elongate member having a second lumen, wherein the second elongate member is positioned external to the elongate member, and delivering the suture through the second lumen. In one or more embodiments, the method may further include securing the suture within a recess of the bobbin, and providing a plurality of angled teeth along a bobbin exterior surface, wherein the plurality of angled teeth is positioned proximate the recess. In one or more embodiments, the method may further include rotatably coupling a pin of the bobbin to the set of support arms, wherein rotation via the plurality of angled teeth causes the suture to spool about a spooling section of the bobbin. In one or more embodiments, the method may further include securing a first free end of the body to a second free end of the body by engaging a plurality of locking features extending from a surface of the second free end with a locking protrusion extending from the first free end. In one more embodiments, the method may further include coupling the body to the proximal end of the elongate member.

In one or more embodiments, a method may include inserting a ligator into a gastrointestinal tract of a patient, the ligator including an elongate member having a lumen, and a ligating band dispenser extending from a distal end of the elongate member. The ligating band dispenser may include a cap, and at least one ligating band positioned on the cap. The ligator may further include an actuation device extending around the elongate member. The actuation device may further include a body defining a central cavity for receiving the elongate member, and a bobbin coupled to the body by a set of support arms. The ligator may further include a suture coupled between the bobbin and the at least one ligating band. The method may further include engaging a target tissue within the gastrointestinal tract of the patient with the ligator, and deploying the at least one ligating band from the cap by rotating the bobbin to draw the suture towards a proximal end of the elongate member, wherein the at least one ligating band is deployed onto the target tissue. In some embodiments, the method may further include drawing the suture through a second lumen of a second elongate member, wherein the second elongate member is positioned external to the elongate member. In some embodiments, the method may further include rotating the bobbin about a pin coupled to the set of support arms, wherein rotation of the bobbin causes the suture to spool about a spooling section of the bobbin. In some embodiments, the method may further include preventing rotation of the bobbin relative to the body, in one direction, using at least one stop operable to engage a plurality of angled teeth extending from the bobbin. In some embodiments, the method may further include securing a first free end of the body to a second free end of the body by engaging a plurality of locking features extending from a surface of the second free end with a locking protrusion extending from the first free end.

Various one or more of the features summarized above may be interchanged, exchanged, combined or substituted with or for other features summarized above, for use in connection with the medical systems and methods summarized above, and with respect to the embodiments described in greater detail below and embodiments otherwise within the scope of the present disclosure.

BRIEF DESCRIPTION OF THE DRAWINGS

Non-limiting embodiments of the present disclosure are described by way of example with reference to the accompanying figures, which are not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. Furthermore, some of the figures include cross-sectional views in the form of "slices", or "near-sighted" cross-sectional views, omitting certain background lines or features otherwise visible in a "true" cross-sectional view, for illustrative clarity. In the figures.

DETAILED DESCRIPTION

The present disclosure is not limited to the particular embodiments described herein. The terminology used herein is for the purpose of describing particular embodiments only, and is not intended to be limiting beyond the scope of the appended claims. Unless otherwise defined, all technical terms used herein have the same meaning as commonly understood by one of ordinary skill in the art to which the disclosure belongs.

As described above, it would be desirable to have an apparatus that would enable a medical professional to both maneuver an endoscope and activate release of elastic bands from a ligator. Disclosed herein are ligators, actuation devices, and methods for deploying ligation bands around a portion of tissue, such as a hemorrhoid, utilizing an endoscope for suction, visualization, and support. The ligators, actuation devices, and methods of the present disclosure advantageously provide a simplified operator interface, which reduces treatment time.

In some embodiments, a ligator may include an elongate member having a lumen, and a ligating band dispenser extending from a distal end of the elongate member. The ligating band dispenser may include a cap and at least one ligating band positioned on the cap. The ligator may further include an actuation device extending around the elongate member, wherein the actuation device includes a body defining a central cavity for receiving the elongate member, at least one support extending into the central cavity from the body, and a bobbin coupled to the body by a set of support arms. A suture may be coupled between the bobbin and the at least one ligating band, wherein rotation of the bobbin draws the suture towards a proximal end of the elongate member, thereby deploying the at least one ligating band from the cap.

In some embodiments, the bobbin of the actuation device may be rotated from a start position to an end position beyond which further rotation is not possible because of the presence of a stop element. When the bobbin reaches the end position, the ligating band dispenser may cause deployment of a single elastic band from the cap.

Figure 1:
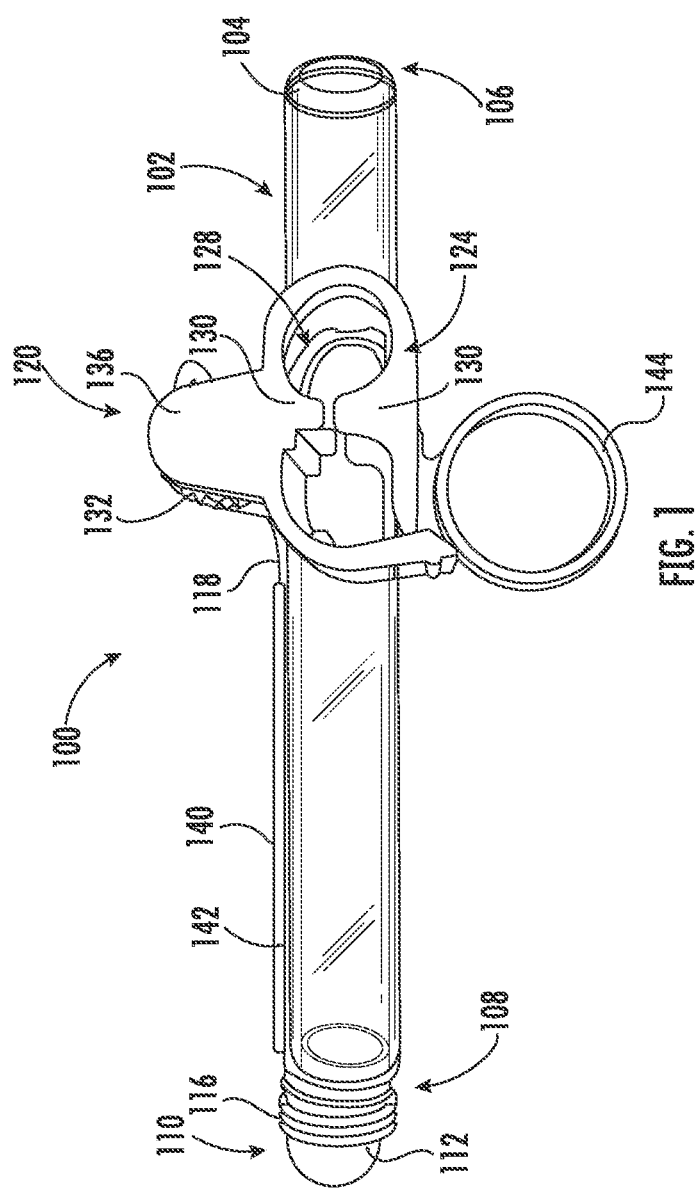
FIGS. 1-2 are perspective views of a ligator according to embodiments of the present disclosure.
Figure 2:
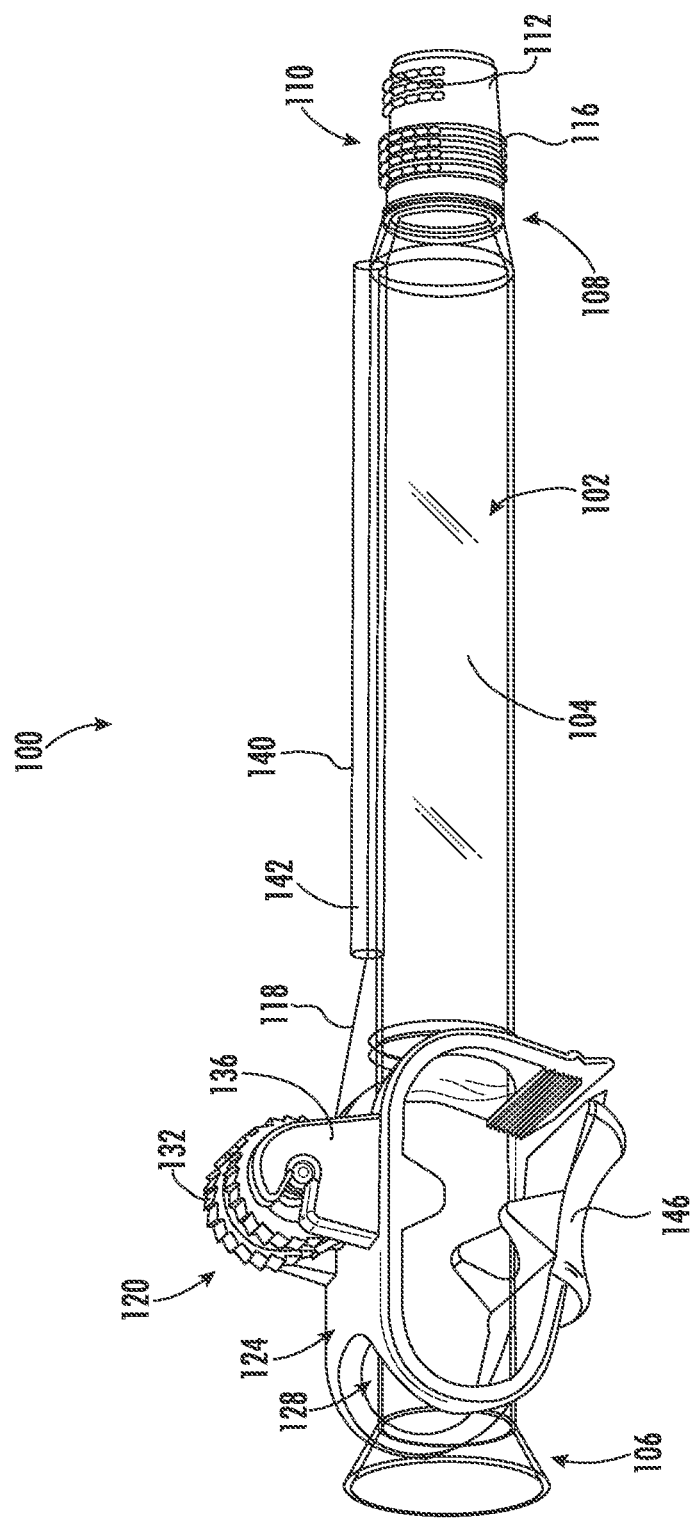

Turning now to FIGS. 1-2, a ligator 100 according to embodiments of the disclosure will be described in greater detail. As shown, the ligator 100 may include an elongate member 102, such as a clear hollow tube, defining a lumen 104. The elongate member 102 includes a proximal end 106 opposite a distal end 108. During use, the elongate member 102 may extend over a distal end of an endoscope (not shown) to provide treatment to a patient. In some embodiments, a length of the elongate member 102 may generally match the length of the endoscope. However, the elongate member 102 may be longer or shorter in various embodiments. In some embodiments, the elongate member 102 may be a flexible material, such as silicone, a thermoplastic elastomer including polyamide and polyether backbone blocks, polyurethane, etc., to allow for scope flexing. In other embodiments, the elongate member 102 may be a rigid material, such as polycarbonate, acrylonitrile butadiene styrene (ABS), etc., to provide a more direct positioning response.

The ligator 100 may further include a ligating band dispenser (hereinafter "dispenser") 110 extending from the distal end 108 of the elongate member 102. As will be described in greater detail below, the dispenser 110 may include a cap 112 and a plurality of ligating bands 116 positioned on the cap 112. The ligating bands 116 may be stretched in an expanded shape to fit on the cap 112 and to maintain positioning until deployment. Although non-limiting, the cap 112 may be made from a polycarbonate or other similar material, and the plurality of ligating bands 116 may each be a loop of rubber. During operation, the plurality of ligating bands 116 may be released by the drawing of a pull line or suture 118 such that the band contracts to engage and isolate targeted tissue. When deployed, the band may cut off blood flow to the targeted tissue such that the tissue will shrink, die, and eventually separate from surrounding tissue. The use of the plurality of ligating bands 116 may allow the ligator 100 to be repositioned for capturing additional tissue with sequential deployment of the plurality of ligating bands 116 without having to withdraw the ligator 100 from the patient. In some embodiments, the dispenser 110 may be coupled to the distal end 108 of the elongate member 102 using a variety of techniques, such as by mechanical fasteners, glue, suture, press fit, tape, overmolding, etc. In other embodiments, the dispenser 110 may be integrally formed with the elongate member 102. Embodiments herein are not limited in this context.

The ligator 100 may further include an actuation device 120 extending around the elongate member 102, wherein the suture 118 is coupled between the actuation device 120 and the dispenser 110. As shown, the actuation device 120 may be positioned proximate to the proximal end 106 of the elongate member 102. Actuation of the actuation device 120 may draw the suture 118 towards the proximal end 106 of the elongate member 102.

In some embodiments, the actuation device 120 may include a body 124 defining a central cavity 128 for receiving the elongate member 102. One or more supports 130 of the body 124 may extend into the central cavity 128. A spool or bobbin 132 may be coupled to the body 124 by a set of support arms 136, wherein rotation of the bobbin 132 draws the suture 118 towards the proximal end 106 of the elongate member 102 to deploy one or more of the plurality of ligating bands 116.

As further shown, the ligator 100 may also include a second elongate member 140 defining a second lumen 142. The suture 118 may extend through the second lumen 142, between the bobbin 132 of the actuation device 120 and the dispenser 110. During use, the suture 118 can move freely within the second lumen 142 in response to rotation of the bobbin 132. Although not shown, the suture 118 may include a series of knots used for anchoring and moving the plurality of ligating bands 116 from the outside of the cap 112 during band deployment.

In some embodiments, the second elongate member 140 is positioned external to the elongate member 102, wherein the first and second elongate members 102, 140 may be secured together using any variety of techniques, for example, mechanically, heat-shrinking, or tape. In other embodiments, the second elongate member 140 may be positioned within the lumen 104. In yet other embodiments, the suture 118 may extend through the first elongate member 102 without the presence of the second elongate member 140.

In some embodiments, as shown in FIG. 1, the body 124 of the actuation device 120 may include a gripping ring 144 extending from to aid the operator when holding the ligator 100. In other embodiments, as shown in FIG. 2, the body 124 may include a contoured finger grip 146 on an underside thereof. Embodiments herein are not limited in this context.

During use, an operator of the ligator 100 may target hemorrhoid tissue by looking through a distal opening in the cap 112 of the dispenser 110 using, for example, an endoscopic camera. Suction may then be applied to bring the target hemorrhoid tissue into the cap 112. The operator may then deploy the plurality of ligating bands 116, for example using only one hand, by rolling the bobbin 132 while simultaneously continuing to hold suction. The bobbin 132 reels-up the suture 118 connected to the cap 112, thereby causing one of the plurality of ligating bands 116 to roll off the distal end of the cap 112 and strangulate the target hemorrhoid tissue within the cap 112. Suction may then be released, and the proper positioning of the ligating band confirmed, for example, by visualizing the site with the endoscope.

In non-limiting embodiments, the actuation device 120 may be calibrated such that a pre-set amount of actuation by the bobbin 132 of the actuation device 120 pulls just enough of the suture 118 to deploy only one of the plurality of ligating bands 116. Releasing the actuation device 120 may then reset the ligator 100 for the next deployment. Actuating the actuation device 120 may again pull just enough of the suture 118 to cause deployment of the next ligating band of the plurality of ligating bands 116. In this manner, the plurality of ligating bands 116 are deployed sequentially.

Figure 3:
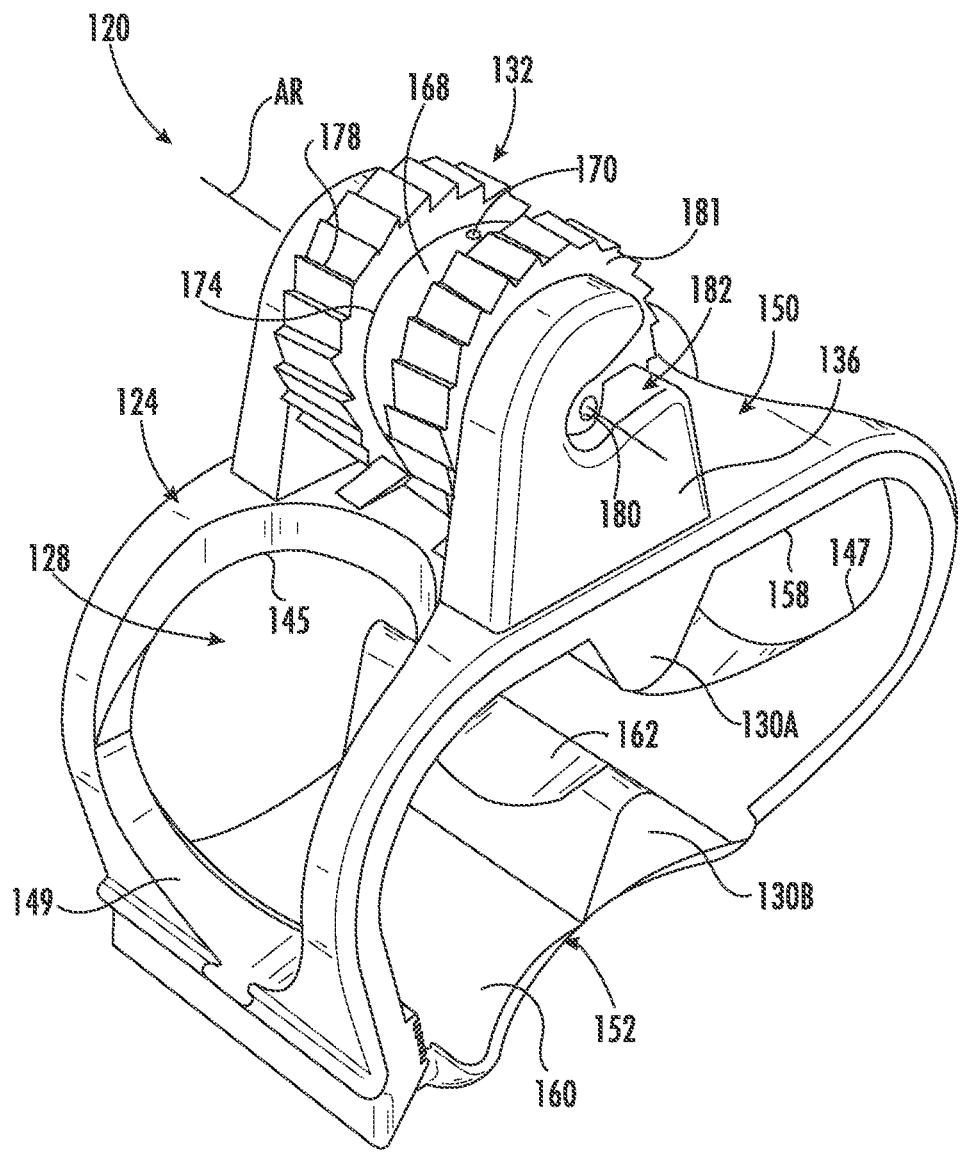
FIG. 3 is a perspective view of an actuation device of the ligator of FIGS. 1-2 according to embodiments of the present disclosure.
Figure 4:
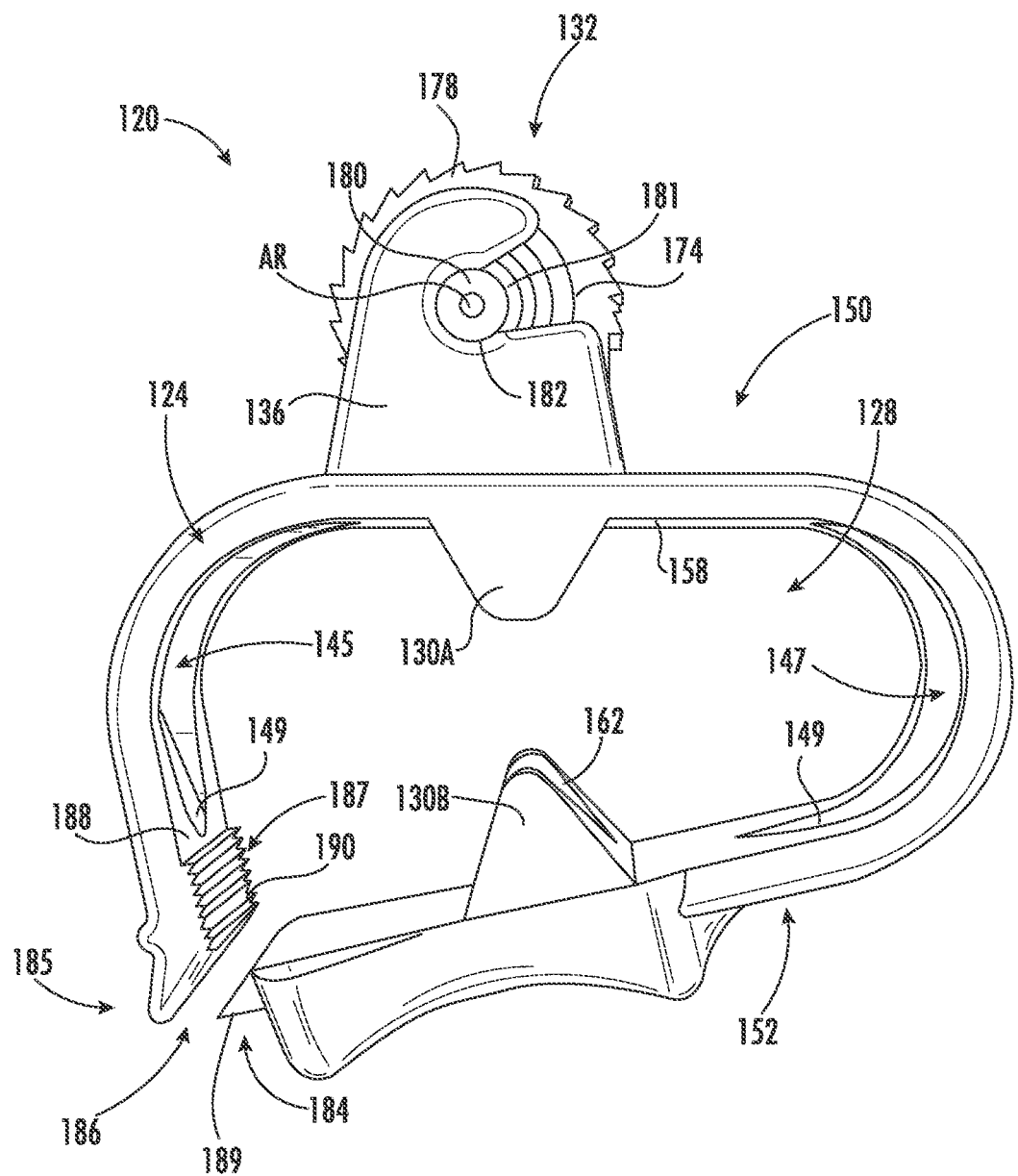
FIG. 4 is a side view of the actuation device of FIG. 3 according to embodiments of the present disclosure.

Turning now to FIGS. 3-4, the actuation device 120 according to embodiments of the present disclosure will be described in greater detail. As shown, the actuation device 120 includes the body 124 defining the central cavity 128 for receiving the elongate member (FIGS. 1-2). The body 124 may include a first opening 145 and a second opening 147. Once assembled, the elongate member may extend through the first and second openings 145, 147. In some embodiments, the body 124 may include one or more receiving surfaces 149 proximate the first and second openings 145 and 147, wherein the receiving surfaces 149 are operable to engage the exterior of the elongate member. The receiving surfaces 149 may increase the surface area at an interface between the body 124 and the elongate member.

As further shown, the body 124 may include a first side 150 opposite a second side 152. An inner surface 158 of the first side 150 may include a first support 130A, while an inner surface 160 of the second side 152 may include a second support 130B. Together the first and second supports 130A-130B engage the elongate member on opposite sides thereof to minimize movement (e.g., axial, radial, rotational) of the elongate member within the body 124. As a result, the body 124 and the elongate member can move together as one singular unit. In some embodiments, one or both of the first and second supports 130A-130B may include a contoured surface 162 configured to generally match dimensions of an exterior surface of the elongate member. The contoured surface(s) 162 may support and further minimize movement of the elongate member within the body 124.

The actuation device 120 may further include the bobbin 132 coupled to the body 124 by the set of support arms 136. As shown, the bobbin 132 may include a spooling section 168 including a recess 170, wherein the suture (not shown) is receivable and securable within the recess 170. In other embodiments, the suture may be coupled to the bobbin 132 using any variety of alternative means.

As further shown, the bobbin 132 may include a plurality of angled teeth 178 extending from a bobbin exterior surface 174. As shown, the plurality of angled teeth 178 may extend circumferentially around the bobbin exterior surface 174. During actuation of the actuation device 120, an operator may engage the plurality of angled teeth 178 with his or her thumb to rotate the bobbin 132. Although non-limiting, the plurality of angled teeth 178 may extend along opposite sides of the spooling section 168. In some embodiments, the spooling section 168 may be recessed relative to the plurality of angled teeth 178 so as to prevent interference between the operator's thumb and the suture 118 during spooling.

The bobbin 132 may further include one or more pins 180 extending from a bobbin sidewall 181. As shown, the pins 180 generally extend along an axis of rotation 'AR,' and are rotatably coupled within one or more slots 182 of the set of support arms 136. In some embodiments, the pins 180 of the bobbin 132 may be press-fitted into the slot(s) 182.

As better shown in FIG. 4, the body 124 of the actuation device 120 may include a first free end 184 proximate a second free end 185. In a first configuration, the first free end 184 and the second free end 185 may be separated from one another by a gap 186. In a second, locked configuration, the first free end 184 may be secured to the second free end 185 by a plurality of locking features 187 extending from an inner surface 188 of the second free end 185. In some embodiments, the first free end 184 may include a locking protrusion 189 operable to extend into a cavity 190 defined by two adjacent locking features of the plurality of locking features 187. The locking protrusion 189 may be a jut or triangular shaped component dimensioned to engage the two adjacent locking features defining the cavity 190. Once engaged with the plurality of locking features 187, the locking protrusion 189 prevents the first free end 184 and the second free end 185 from separating.

The first free end 184 and the second free end 185 may be locked and/or unlocked by any mechanical fasteners such that the actuation device 120 may be coupled to an elongate member 102 and held in position during a ligation procedure. In some embodiments, the body 124 may be formed as a single, continuous member, and may be attached as a friction fit (e.g., heat-shrink) to the elongate member 102.

Figure 5:
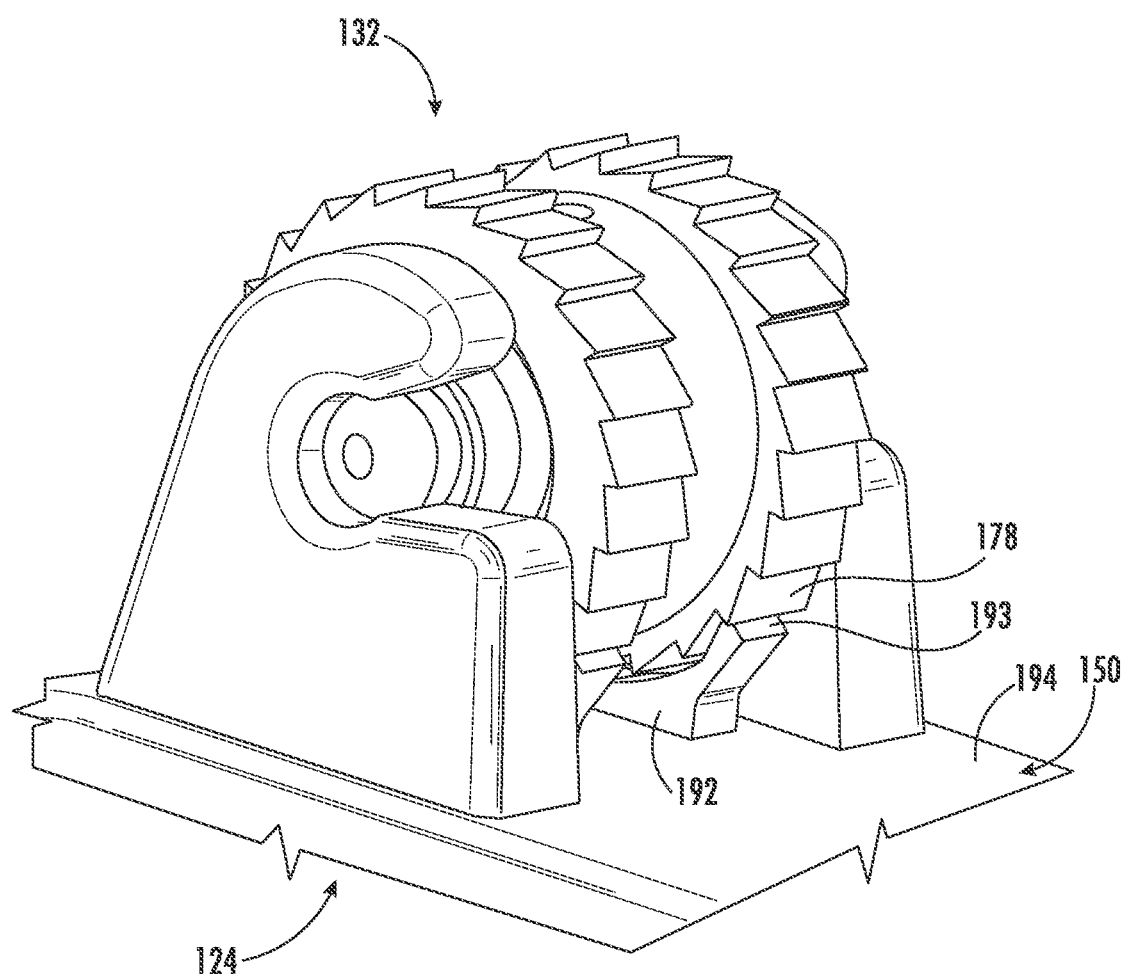
FIG. 5 is a perspective view depicting operation of the bobbin of the actuation device according to embodiments of the present disclosure.

Turning now to FIG. 5, operation of the bobbin 132 of the actuation device 120 according to embodiments of the present disclosure will be described in greater detail. As shown, the bobbin 132 and the body 124 of the actuation device 120 may function as a ratchet, allowing motion in one direction only. For example, the body 124 may include one or more stops 192 extending from an upper surface 194 of the first side 150. The stops 192 may include a face 193 operable to engage a corresponding surface of one of the plurality of angled teeth 178 of the bobbin 132. Because the plurality of angled teeth 178 are inclined or slanted, the bobbin 132 may rotate only in a counter-clockwise direction. In other embodiments, the incline or slant of the plurality of angled teeth 178 may be reversed, thus allowing rotation of the bobbin in a clockwise direction. Embodiments of the present disclosure are not limited in this context.

Figure 6:
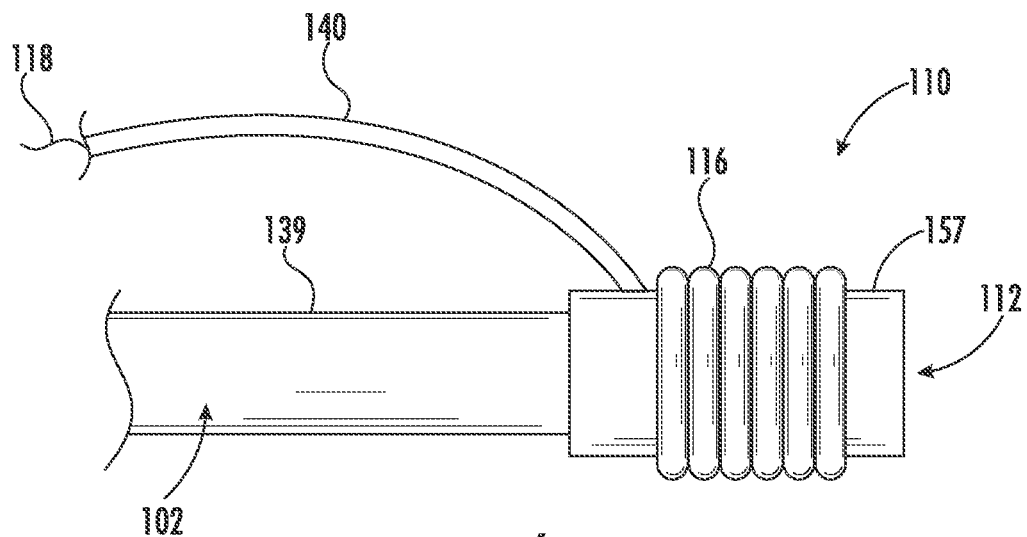
FIG. 6 is a side view of a distal end of the ligator according to embodiments of the present disclosure.
Figure 7:
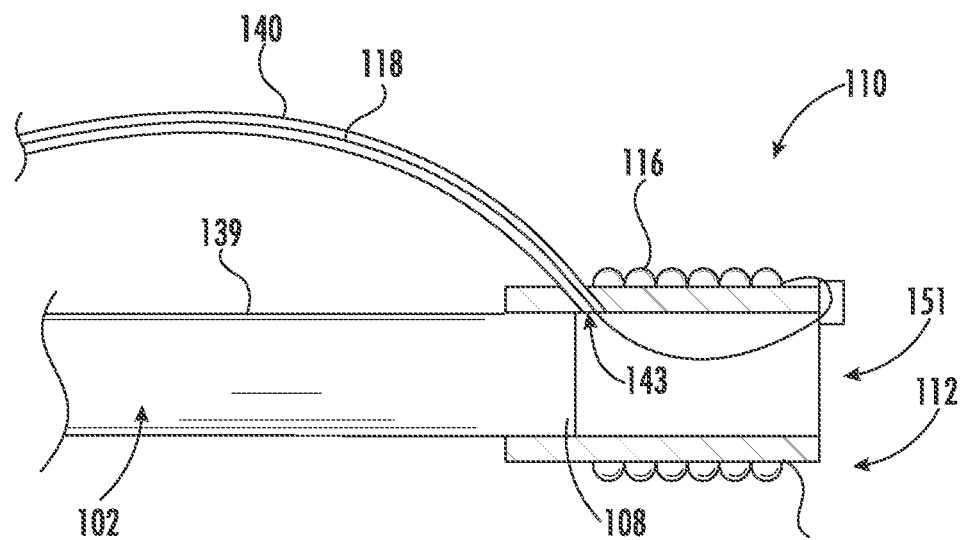
FIG. 7 is a detailed cross-sectional view of the distal end of the ligating instrument of FIG. 6 according to embodiments of the present disclosure.

FIGS. 6-7 demonstrate connection of the suture 118 with the dispenser 110 according to non-limiting embodiments of the present disclosure. As shown, the elongate member 102, which may be in the form of a tube, may be coupled to the cap 112 of the dispenser 110. In some embodiments, the cap 112 is press-fitted over an outer surface 139 of the elongate member 102. The suture 118 may extend inside the second elongate member 140. As shown, the suture 118 is connected to one or more ligating bands 116 extending around an exterior surface 157 of the cap 112.

As better shown in FIG. 7, the cap 112 may include an aperture 143 through a sidewall thereof, the aperture allowing the suture 118 to exit from a central bore 151 of the dispenser 110. In some embodiments, the aperture 143 is located distal to the distal end 108 of the elongate member 102, for example, when the dispenser 110 is attached to the elongate member 102.

Figure 8:
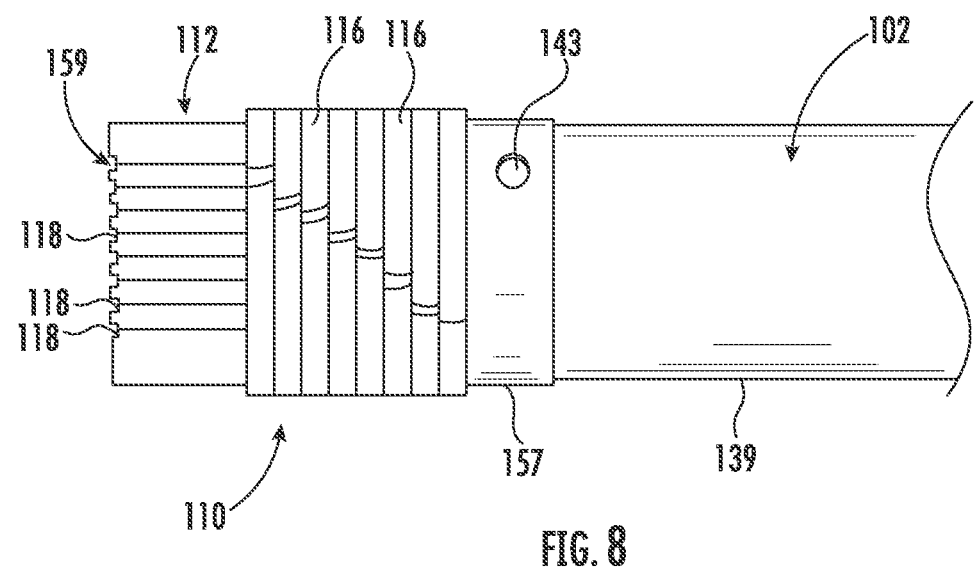
FIG. 8 is a detailed side view of a ligating band dispenser according to embodiments of the present disclosure.

As shown in FIG. 8, the ligating bands 116 may be positioned adjacent one another, around the exterior surface 157 of the cap 112. In the non-limiting embodiment shown, the suture 118 wraps around each of the ligating bands 116, extends across the cap 112 in a back and forth configuration through a plurality of slots 159, and passes into the central bore 151 (FIG. 7). As the suture 118 is pulled through the aperture 143, the suture 118 may release a distal most positioned ligating band 116 from the dispenser 110.

Figure 9:
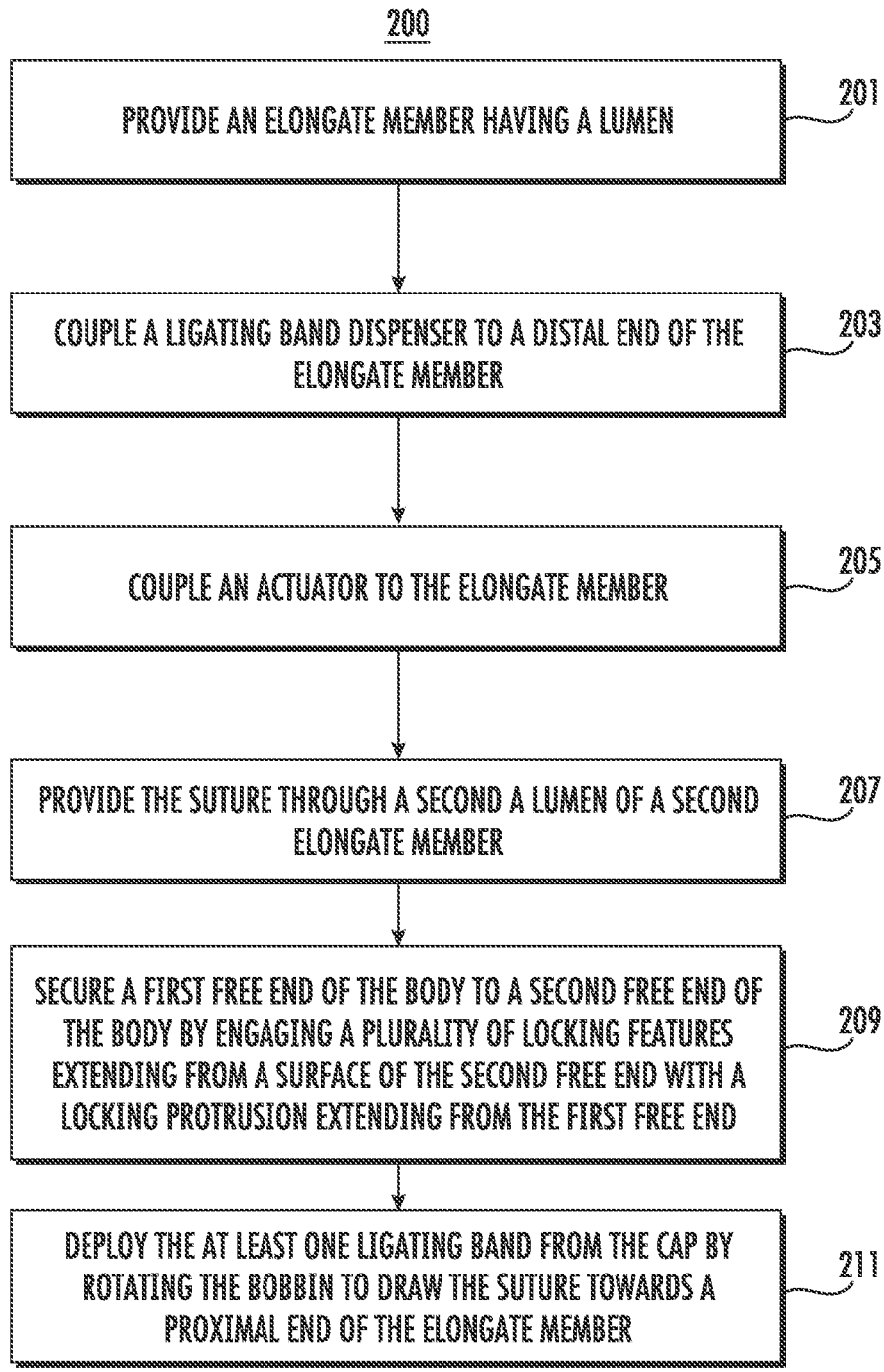
FIG. 9 is a flow diagram of a method according to embodiments of the present disclosure.

FIG. 9 is a flow diagram of a method 200 according to embodiments of the present disclosure. At block 201, the method 200 may include providing an elongate member having a lumen. In some embodiments, the elongate member is a hollow tube operable to extend over an endoscope for treatment of hemorrhoids.

At block 203, the method 200 may include coupling a ligating band dispenser to a distal end of the elongate member. In some embodiments, the ligating band dispenser may include a cap and at least one ligating band positioned on the cap. In some embodiments, the cap may be transparent or translucent, and include an opening at a distal end thereof. During use, the hemorrhoid may be sucked into the cap through the opening for subsequent treatment. It is understood that in some embodiments, the band dispenser may be integrally formed with the elongate member.

At block 205, the method 200 may include coupling an actuation device to the elongate member. In some embodiments, the actuation device may include a body defining a central cavity for receiving the elongate member, and at least one support extending into the central cavity from the body. The actuation device may further include a bobbin coupled to the body by a set of support arms.

In some embodiments, the method 200 may further include securing the suture within a recess of the bobbin, and providing a plurality of angled teeth along a bobbin exterior surface, the plurality of angled teeth positioned proximate the recess. In some embodiments, the plurality of angled teeth may extend circumferentially around the exterior surface. During actuation of the actuation device, an operator may engage the plurality of angled teeth with his or her thumb to more easily rotate the bobbin. In some embodiments, a pin of the bobbin may be coupled to the set of support arms.

At block 207, the method 200 may include coupling a suture between the bobbin and the ligating band dispenser, wherein rotation of the bobbin draws the suture towards a proximal end of the elongate member to deploy the at least one ligating band from the cap. In some embodiments, the suture may be provided through a second lumen of a second elongate member. In some embodiments, the second elongate member is positioned external to the elongate member. In some embodiments, the second elongate member and the elongate member are directly coupled together.

At block 209, the method may optionally include securing a first free end of the body to a second free end of the body by engaging a plurality of locking features extending from a surface of the second free end with a locking protrusion extending from the first free end. In some embodiments, the locking protrusion may be a jut or triangular shaped component operable to extend into a cavity defined by two adjacent locking features of the plurality of locking features. Once engaged with the plurality of locking features, the locking mechanism causes the body to maintain a secure fit with the elongate member.

At block 211, the method 200 may include deploying the at least one ligating band from the cap by rotating the bobbin to draw the suture towards a proximal end of the elongate member. In some embodiments, the actuation device 120 may be calibrated such that actuation of the actuation device pulls just enough of the suture to deploy only one of the plurality of ligating bands. As a result, the plurality of ligating bands may be deployed sequentially.

In some embodiments, a physician may operate the ligator described herein by inserting the ligator into the gastrointestinal tract of a patient, the ligator including the elongate member having the lumen, and the ligating band dispenser extending from the distal end of the elongate member. The ligating band dispenser may include the cap, and at least one ligating band positioned on the cap. The ligator may further include the actuation device extending around the elongate member. The actuation device may further include the body defining the central cavity for receiving the elongate member, and the bobbin coupled to the body by the set of support arms. The ligator may further include the suture coupled between the bobbin and the at least one ligating band.

Next, the physician may engage the target tissue within the gastrointestinal tract of the patient with the ligator, and deploy the at least one ligating band from the cap by rotating the bobbin to draw the suture towards a proximal end of the elongate member. As a result, the at least one ligating band is deployed onto the target tissue.

Although described herein as a ligator attachable over an endoscope, it will be appreciated that other configurations are possible within the scope of the present disclosure. For example, the ligator may be placed over an instrument or object other than an endoscope. Furthermore, the ligator may be self-contained device with or without built-in visualization means. In some embodiments, the ligator may be a single-use device with a camera, ligating band dispenser, and actuator all built-in.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

As used herein, the singular forms "a," "an," and "the" are intended to include the plural forms as well, unless the context clearly indicates otherwise. It will be further understood that the terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

Furthermore, the terms "substantial" or "substantially," as well as the terms "approximate" or "approximately," can be used interchangeably in some embodiments, and can be described using any relative measures acceptable by one of skill. For example, these terms can serve as a comparison to a reference parameter, to indicate a deviation that will still provide the intended function. Although non-limiting, the deviation from the reference parameter can be, for example, in an amount of less than 1%, less than 3%, less than 5%, less than 10%, less than 15%, less than 20%, and so on.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Still furthermore, although the illustrative method 200 is described above as a series of acts or events, the present disclosure is not limited by the illustrated ordering of such acts or events unless specifically stated. For example, some acts may occur in different orders and/or concurrently with other acts or events apart from those illustrated and/or described herein, in accordance with the disclosure. In addition, not all illustrated acts or events may be required to implement a methodology in accordance with the present disclosure.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A ligator comprising:
   an elongate member having a distal end and a proximal end, a lumen therethrough extending between the distal end and the proximal end and sized to receive a distal end of an endoscope, and having an exterior surface between the distal end and the proximal end sized for positioning within a body of a patient;
   a ligating band dispenser extending from the distal end of the elongate member, the ligating band dispenser comprising:
     a cap; and
     at least one ligating band positioned on the cap;
   an actuation device extending around and engaging the exterior surface of the elongate member proximate yet distal to the proximal end of the elongate member, the actuation device comprising:
     a body defining a central cavity dimensioned for receiving the exterior surface of the elongate member; and a bobbin coupled to the body by a set of support arms; and a suture coupled between the bobbin and the at least one ligating band, wherein rotation of the bobbin draws the suture towards the proximal end of the elongate member to deploy the at least one ligating band from the cap.

2. The ligator of claim 1, further comprising a second elongate member having a second lumen extending along the lumen of the elongate member, wherein the suture extends through the second lumen.

3. The ligator of claim 2, wherein the second elongate member is positioned external to the elongate member.

4. The ligator of claim 1, further comprising an endoscope, wherein the lumen of the elongate member is sized to receive a distal shaft of the endo scope, and the actuation device is mounted on the proximal end of the elongate member distal to a handle of the endo scope.

5. The ligator of claim 1, the bobbin comprising:
   a spooling section including a recess, wherein the suture is received within the recess;
   a plurality of angled teeth extending along a bobbin exterior surface, wherein the plurality of angled teeth is disposed adjacent the spooling section; and
   a pin extending from a bobbin sidewall, wherein the pin extends along an axis of rotation of the bobbin, and wherein the pin is rotatably coupled with the set of support arms.

6. The ligator of claim 1, the actuation device further comprising at least one support extending into the central cavity from the body, the at least one support comprising a contoured surface engaged with the exterior surface of the elongate member.

7. The ligator of claim 1, the actuation device further comprising a first free end secured to a second free end by a plurality of locking features extending from a surface of the second free end.

8. The ligator of claim 7, wherein the first free end comprises a locking protrusion operable to extend into a cavity defined by two adjacent locking features of the plurality of locking features.

9. The ligator of claim 1, the actuation device further comprising a gripping ring extending from an underside of the body.

10. The ligator of claim 1, wherein the at least one ligating band comprises a plurality of ligating bands positioned on the cap for sequential deployment therefrom.

11. The ligator of claim 1, wherein the suture is wrapped around the at least one ligating band such that drawing of the suture toward the proximal end of the elongate member causes the ligating band to be pulled distally off the distal end of the elongate member.

12. A method, comprising:
   inserting an elongate member of a ligator into a gastrointestinal tract of a patient, the elongate member having a distal end and a proximal end and an exterior surface extending from said distal end to said proximal end sized for positioning within the gastrointestinal tract of the patient, the ligator further including:
      a ligating band dispenser extending from the distal end of the elongate member and including:
         a cap; and
         at least one ligating band positioned on the cap; and
      an actuation device extending around and engaging the exterior surface of the elongate member proximate yet distal to the proximal end of the elongate member, the actuation device including:
         a body defining a central cavity for receiving the elongate member;
         a bobbin coupled to the body by a set of support arms; and
         a suture coupled between the bobbin and the at least one ligating band;
   engaging a target tissue within the gastrointestinal tract of the patient with the ligator; and
   deploying the at least one ligating band from the cap by rotating the bobbin to draw the suture towards the proximal end of the elongate member to pull the at least one ligating band distally off the cap to be deployed onto the target tissue.

13. The method of claim 12, further comprising drawing the suture through a lumen of a second elongate member, wherein the second elongate member is positioned external to the elongate member.

14. The method of claim 12, further comprising rotating the bobbin about a pin coupled to the set of support arms, wherein rotation of the bobbin causes the suture to spool about a spooling section of the bobbin.

* * * * *